United States Patent
Johnson, Jr.

[11] 3,955,565
[45] May 11, 1976

[54] ORTHOPEDIC APPARATUS

[76] Inventor: Glenn W. Johnson, Jr., 10 Friar Tuck Circle, Summit, N.J. 07901

[22] Filed: Dec. 5, 1973

[21] Appl. No.: 421,747

[52] U.S. Cl. .................... 128/89 R; 128/DIG. 20
[51] Int. Cl.² ............................................ A61F 5/04
[58] Field of Search .......... 128/89, 87, 90, DIG. 20, 128/83

[56] References Cited
UNITED STATES PATENTS

| | | | |
|---|---|---|---|
| 323,775 | 8/1885 | Bender et al. | 128/89 R |
| 392,157 | 10/1888 | Lee | 128/89 R |
| 432,899 | 7/1890 | Reenstierna | 128/89 R |
| 458,804 | 9/1891 | Ellis | 128/89 R |
| 2,682,869 | 7/1954 | Papp | 128/87 R |
| 3,631,855 | 1/1972 | Fehlau | 128/90 |
| 3,643,656 | 2/1972 | Young et al. | 128/DIG. 20 |
| 3,701,349 | 10/1972 | Larson | 128/89 R |
| 3,760,056 | 9/1973 | Rudy | 128/90 |
| 3,800,789 | 4/1974 | Schloss | 128/90 |

FOREIGN PATENTS OR APPLICATIONS

| | | | |
|---|---|---|---|
| 1,233,172 | 5/1971 | United Kingdom | 128/90 |
| 590,333 | 1/1960 | Canada | 128/90 |
| 470,174 | 5/1969 | Switzerland | 128/DIG. 20 |
| 1,325,526 | 12/1963 | France | 128/83 |

*Primary Examiner*—John D. Yasko

[57] ABSTRACT

In accordance with the invention, there is provided a pair of complementary shaped half-shell members fabricated from a tough, relatively thin material such that each half-shell member is substantially flexible about its longitudinal axis yet is substantially rigid about a transverse axis perpendicular to its longitudinal axis. The half-shell members are adapted to be receivably engaged with respect to each other in a diametrically opposed concentric nesting fashion and due to their inherent radial flexibility may be adjusted relative to each other to form a radially telescoped generally cylindrically shaped outer shell structure of selective inside diameter generally conforming to the shape of an injured limb such as, for example, a leg or arm. Disposed interiorly of the outer shell structure is a series of air bags or similar means capable of assuming a normally flattened configuration but which when inflated with air through a valved inlet port are capable of being radially expanded to conform to the irregular shape of the limb or other body part with which each air bag is intended to engage. Means are provided for firmly releasably securing the radially telescoped half-shell members together after they have been snugly fitted relative to each other about the limb or other body part. In an alternatively preferred form of the invention, the two complementary half-shell members are configured to form an outer shell structure conforming generally to the shape of a pair of articulated or conjoint body limbs whereby the two articulated or conjoined limbs are immobilized with respect to each other.

18 Claims, 10 Drawing Figures

ORTHOPEDIC APPARATUS

The present invention relates generally to orthopedic devices, and more particularly, to those orthopedic devices known variously as casts, splints, braces, etc. which are especially adapted for immobilizing and/or protecting injured limbs or other parts of the anatomy, either human or animal.

It has long been desirable to replace the conventional plaster of paris cast with a device that among other advantages is light in weight, easily applied about an injured limb or other body part, reusable without being destroyed, and capable of periodic adjustment so as to conform to the changing size of the injured limb or other body part with which it is being used. One such device is disclosed, for example, in the U.S. patent to Larson, U.S. Pat. No. 3,701,349, and comprises a pair of rigid plastic shell members adapted to be releasably secured in enclosing relation about a damaged limb. Inside and extending coextensively with each rigid shell member there is disposed a flexible liner capable of being inflated by a suitable medium, say air, for example, introduced through a valve or inlet port to provided a constant pressure support means conforming to the irregular shape of the limb around which it engages. According to the teachings in the patent, by regulating the pressure within the inflatable liners suitable adjustment can be made to compensate for swelling and contraction of the damaged limb, or to achieve optimum body comfort for the wearer of the device.

While it is apparent that the device described in the aforementioned patent does offer considerable advantages over a conventional plaster cast, it still suffers from certain disadvantages. For example, in the cast described in the Larson patent the two rigid half-shell members are releasably secured together along complementary abutting surfaces to form a hollow substantially cylindrical outer shell, the inside diameter of which is substantially greater than the largest outside diameter of the injured limb. Since each half-shell member includes a single inflatable liner, the damaged limb is directly supported by a two-part annular "air cushion" in the clearance space formed between the relatively regularly shaped interior of the cylindrical shell and the irregularly shaped surface contour of the injured limb. Even at relatively high inflation pressures, however, it is still possible for the damaged limb to move or be displaced relative to and within the outer shell notwithstanding the constant pressure support provided by the two inflated liners. The reason for this is that ideally, each inflated liner should form a dimensionally stable, relatively stiff "air-spring" which when compressed will offer increasing resistance to further displacement. However, the air cushions provided by the two inflated liners in the Larson cast being coextensive with each half-shell member respectively, are so relatively large in terms of their transverse and longitudinal extent that any loading of the inflated liner that is not directed substantially against the central portions thereof rather than being resisted by a firm compressive counterforce will merely displace air from one end of the liner to the other end of the same liner. Stated otherwise, the extreme longitudinal and transverse portions of the inflated liners in the Larson cast are incapable of providing the same support against displacement of the limb encased therein as are the central portions of the liner which may be quite adequate in this regard.

As a result, with respect to stresses imposed on the shell or the limb which might tend to induce relative displacement of the limb in a direction parallel to and generally toward the longitudinally extending abutting surfaces of the two half-shell members, the inflated liners in the prior patented cast offer little or no pressure support or resistance against such displacement since it is along these seams that the extreme lateral extremities of the two liners abut each other.

Similarly, any stresses imposed on the limb or cast which would tend to rock the limb about a transverse axis perpendicular to the central longitudinal axis of the cast may cause the limb to "pinch" one or both of the inflated liners relative to the outer shell at say the upper extremity of the cast whereas at the bottom extremity of the cast the opposite side of the other or both liners would be similarly "pinched" thereby offering insufficient support against such rotational displacement of the limb relative to the cast's outer shell member.

The two-part annular air-cushion in the Larson device, therefore, actually comprises a relatively unstable floating suspension for the damaged limb which may be completely effective in preventing undesirable displacements of the damaged limb relative to the cylindrical outer shell member encasing both the annular air-cushion and the limb.

Furthermore, as mentioned above, a significant feature of the prior art device is its ability to conform to the change in size of an injured limb. Such changes are typically contractions of the limb since the swelling attendent the original injury gradually subsides and as the period of immobilization continues the injured limb usually atrophies to an extent. It is apparent that since the inflatable liner is the only adjustable element in the prior art system the disadvantage described above with respect to the instability of the annular air-cushion between the outer shell and the injured limb is compounded when such adjustments are made inasmuch as the greater the annular thickness of the air-cushion between the encased limb and the outer protective shell, the greater is the freedom of and possibility for displacement of the limb relative to the outer shell.

Moreover, since the prior art air-suspension cast comprises a pair of rigid half-shell members defining a hollow cylindrical shell structure having a constant or fixed inside diameter once the device is assembled about an injured limb, the range of adjustment afforded thereby is extremely limited being dependent upon the degree which the inner liner can be extended radially under internal pressure and the maximum inflation pressure that can be tolerated by the wearer of the cast. This means that several different sized shells are required to treat corresponding damaged limbs of relatively disparate size and thus, for example, one size shell would be required to treat a damaged fibula on a small woman whereas a different sized shell member would be required to treat the same injury on a large male.

Against the foregoing background, it is a primary object of the present invention to provide a greatly improved orthopedic device of the air-suspension type which retains all of the advantages of the prior art device yet overcomes each of the disadvantages enumerated above.

It is another object of the present invention to provide an improved orthopedic device of the air-suspension type having an outer protective shell and which is capable of preventing relative displacement between an injured limb or other body part and the outer protective shell in which it is encased.

It is yet another object of the present invention to provide an improved orthopedic device of the air-suspension type having an outer protective shell and which includes means for selectively adjusting the inside diameter of the outer shell over a relatively wide range whereby a single standard sized device may be used to effectively immobilize corresponding injured limbs or other body parts of widely varying size.

It is still another object of the present invention to provide an improved orthopedic device of the air-suspension type having an outer protective shell formed by a pair of corresponding half-shell members whereby the two half-shell members are slidably engagable with respect to each other in a radially telescoping manner.

It is yet still another object of the present invention to provide an orthopedic device of the air-suspension type having improved means for ventilating the interior thereof when worn about an injured limb or other body part.

It is yet another object of the present invention to provide an improved orthopedic device capable of immobilizing a pair of articulated limbs or other body parts relative to each other thereby providing means for treating an injured joint connecting the articulated limbs or other body parts.

Toward the accomplishment of these and additional objectives and advantages, the present invention, briefly summarized, comprises a pair of complementary shaped half-shell members fabricated from a tough, relatively thin material such that each half-shell member is substantially flexible about its longitudinal axis yet is substantially rigid about a transverse axis perpendicular to its longitudinal axis. The half-shell members are adapted to be receivably engaged with respect to each other in a diametrically opposed concentric nesting fashion and due to their inherent radial flexibility may be adjusted relative to each other to form a generally cylindrically shaped outer shell structure of selective inside diameter generally conforming to the shape of an injured limb such as, for example, a leg or arm. Disposed interiorly of the outer shell structure is a series of air bags or similar means capable of assuming a normally flattened configuration but which when inflated with air through a valved inlet port are capable of being radially expanded to conform to the irregular shape of the limb or other body part around which each air bag is in engaging contact. In operation, the half-shell members are positioned diametrically about an injured limb or body part and are receivably engaged with respect to each other in a generally radially telescoping manner about the injured limb until each half-shell member is in snug abutting engagement with the injured limb at at least one axial location and preferably at a pair of spaced axial or longitudinal locations with respect to the limb. The half-shell members are then firmly releasably secured relative to each other by suitable means such as a series of circumferentially extending strips of VELCRO fastening material, for example. Finally, the air bags are inflated until they fill the voids between the protective outer shell formed by the two diametrically opposed radially telescoping half-shell members and those portions of the limb which are not in snug abutting engagement with each half-shell member.

In an alternate preferred form of the present invention, the two complementary half-shell members are configured to form an outer shell structure conforming generally to the shape of a pair of articulated or conjoint body limbs whereby the two articulated or conjoined limbs are immobilized with respect to each other.

The foregoing and still other features and advantages as well as a more complete understanding of the present invention will be made apparent from a study of the following detailed description of the invention in connection with the accompanying drawings wherein.

Figure 1A:
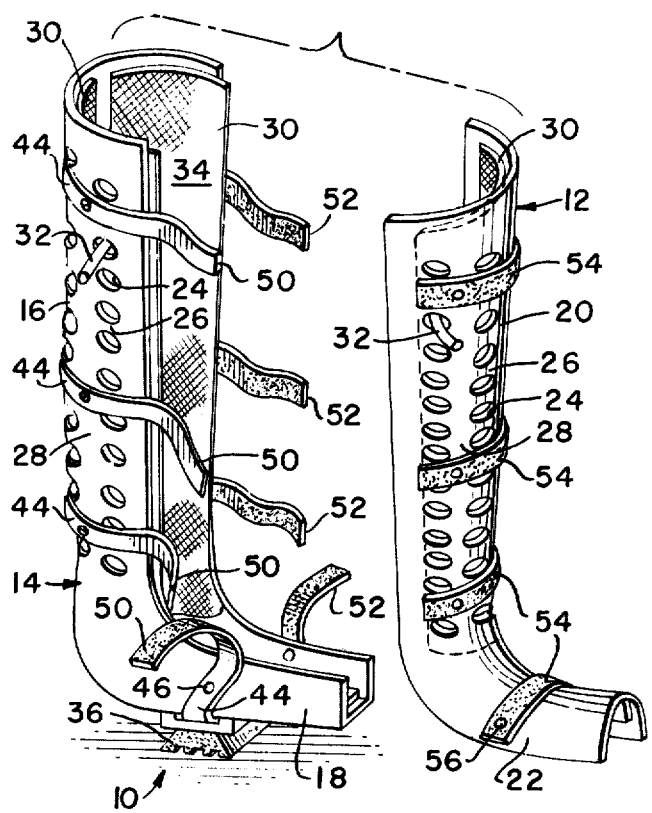
FIG. 1A is a perspective view of a preferred embodiment of the invention, in particular, a walking cast suitable for treating an injured lower leg, showing the cast in unassembled condition.

Referring now to the drawings wherein like reference numerals represent like parts throughout, and initially to FIGS. 1 - 6, there is shown as illustrative of one preferred form of the invention a walking cast generally indicated by reference numeral 10 and which is particularly adapted for treating injuries to the lower leg e.g., medial fractures of the fibula or tibia.

Figure 1B:
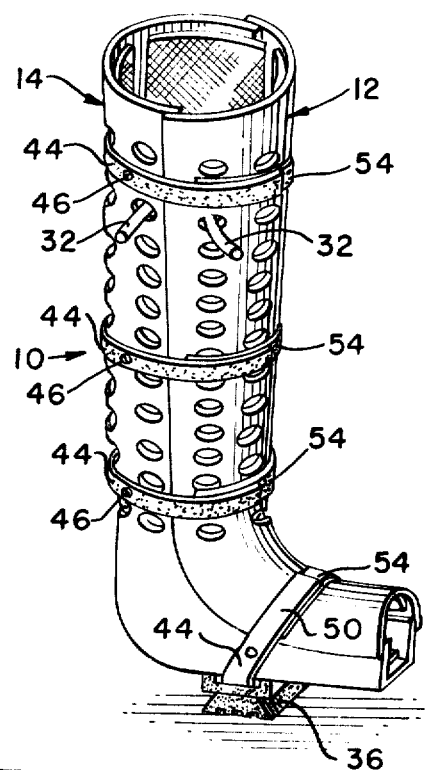
FIG. 1B is a perspective view showing the walking cast of FIG. 1A in assembled condition, but not showing the cast in engagement with a lower leg.
Figure 2:
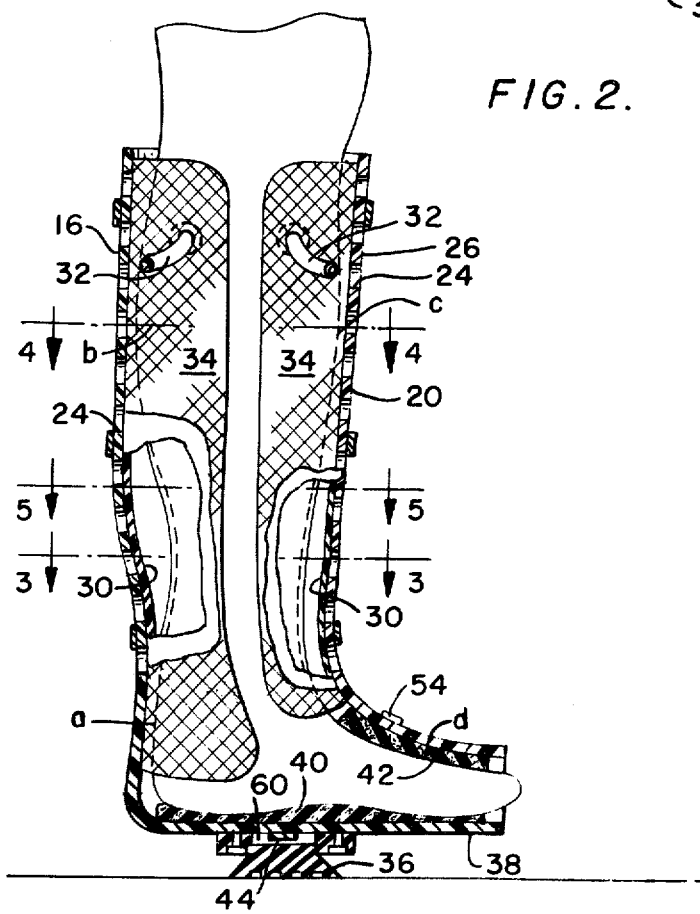
FIG. 2 is a sectional view in elevation showing the assembled cast of FIG. 1B in engagement with a lower leg.

Cast 10 comprises a pair of complementary, cooperating half-shell members 12, 14 each of which generally conforms to the shape of the foot and lower leg. Thus, each half-shell member essentially has a channel shaped or semi-cylindrical cross-sectional configuration and is generally formed in the shape of an "L" as shown in FIGS. 1A, 1B, and 2. The vertically extending or upright portion 16 of shell member 14 conforms generally to the rear of the lower leg whereas the lower horizontally extending portion 18 of the shell member 14 conforms generally to the heel and sole portion of the foot. In similar fashion, the vertically extending or upright portion 20 of the half-shell member 12 generally conforms to the front of the lower leg while the lower horizontally extending portion 22 of the shell member 12 generally conforms to the upper or instep portion of the foot. If desired, half-shell members 12, 14 may have their inside diameters tapered slightly toward their bottommost extremities to conform more closely to the shape of a typical lower leg while similarly, the vertically extending upright portion 20 of half-shell member 14 may be curved slightly in the longitudinal direction (i.e., in the plane of FIG. 2) to conform more closely to the curve of the rear of the calf of the lower leg although this is not absolutely necessary as will appear obvious from the following description.

In accordance with an important feature of the present invention, the individual half-shell members are fabricated from a relatively thin material such that each half-shell member is extremely light in weight and moreover, has the capability of being easily flexed about its longitudinal axis to increase or decrease the inside diameter thereof while being relatively resistant to flexure about a transverse axis perpendicular to its longitudinal axis. While a wide range of known materials may be employed to meet the foregoing requirements, synthetic polymeric resinous materials such as the thermoplastics, for example, are particularly preferred since they are relatively inexpensive, are commercially available from several sources, and can easily be used to form the half-shell members in the shape substantially as shown in FIG. 1A as by vacuum forming, injection molding or other techniques well known in the plastics forming art. Exemplary thermoplastic materials suitable for use in practicing the present invention may be obtained commercially from Rhom and Haas Co. under the trademark KYDEX; General Electric Co. under the trademark LEXAN; Du Pont & Co. under the trademark LUCITE; and Borg-Warner Corporation under the trademark CYCOLAC.

It has been found that when the half-shell members 12, 14 shown in FIG. 1A are formed from such materials having a thickness generally in the range of about 0.030 to about 0.100 inches, the half-shell members are easily flexed about their longitudinal axes respectively, are adequately rigid about a transverse axis perpendicular to said longitudinal axis and together weigh in the neighborhood of about 1.5 to about 3.0 pounds.

In order to reduce still further the weight of the half-shell members 12, 14 they are each preferably provided with a plurality of spaced apart columns of apertures 24 substantially as shown in FIGS. 1A and 1B, the apertures in each column having a common centerline and being preferably equally spaced from one another so as to form a plurality of generally parallel spaced apart rows extending circumferentially with respect to each half-shell member. The apertures 24 comprising each row likewise are preferably equally spaced from one another, the spacing between apertures in each row, however, being generally greater than the spacing between apertures in each column. Since, as mentioned previously, the half-shell members may be tapered somewhat toward their lowermost extremities, respectively, under such circumstances, the various columns of apertures may be arranged in such a manner that the centerlines thereof slightly converge toward each other near the lower portion of each half-shell member. Thus, although the apertures in each row are equally spaced from one another, the spacing between apertures in the lowermost rows will generally decrease at a rate approximately equal to the rate of taper when compared to the spacing of the apertures in the rows disposed in the upper portion of each half-shell member. This arrangement has been found to produce an aesthetically appealing cast. In any event, the provision of a pattern of apertures 24 disposed on each shell member generally comprising a series of evenly spaced columns and rows as described above and as shown in the drawings has been found to reduce the weight of the individual half-shell members and at the same time improves the ability of the half-shell member to flex about its longitudinal axis while minimally affecting the ability of each half-shell member to resist flexure about a transverse axis perpendicular to said longitudinal axis. The reason for this may be more fully appreciated by observing that since the spacing between apertures in each row is greater than the spacing between apertures in each column, the foregoing arrangement actually defines a series of spaced columns of necked-down flexural hinges 26, the columns extending circumferentially with respect to each half-shell member and each flexural hinge 26 having its bending axis parallel to the longitudinal axis of the half-shell member. The longitudinally aligned flexural hinges 26 thus permit each panel 28 defined between adjacent columns thereof to easily flex relative to its neighboring panel about the shell member's longitudinal axis while each panel 28 being arcuately shaped has considerable rigidity about a transverse axis perpendicular to its axis of curvature, that is, in effect it has the rigidity approaching that of a rigid column. Stated otherwise, the plurality of acruately shaped panels 28 defined by and extending between the individual columns of apertures in each shell member may be considered as a series of arcuately shaped longitudinally extending splints hinged to one another by virtue of the flexural hinges formed by the necked-down portions provided between adjacent apertures in each column.

It is emphasized that the preferred arrangement of apertures 24 described above is not absolutely essential to assure the required degree of radial flexibility in each shell member 12, 14 since this may be accomplished merely by forming a sufficiently thin half-shell member. However, by using the preferred arrangement of apertures 24, half-shell members having increased thicknesses may be employed thus assuring adequate rigidity about a transverse axis without affecting the desired ability of the shell member to be freely flexible about a longitudinal axis perpendicular to said transverse axis.

Moreover, as will be more fully explained below, the apertures 24 provided in each half-shell member 12, 14 are further advantageous in that they facilitate ventilation of the interior of the cast 10 in a novel manner according to the present invention.

Half-shell member 12 has concentrically nested interiorly thereof a pneumatic cell or air bag 30 of generally flattened, arcuate configuration conforming to the inside curvature of the shell member. As best seen in FIG. 2, the air bag 30 preferably extends substantially along the full vertical length of the half-shell member and includes an inlet tube or port 32 adapted to extend through one of the apertures 24 in the shell member 12 (see FIGS. 1A and 1B). The inlet tube or port 32 may be fitted with a valve or closure means of known construction for permitting the introduction of an inflating pressure into the interior of the air bag and for maintaining such internal pressure.

Likewise, half-shell member 14 has concentrically nested interiorly thereof a pair of similar air bags 30 extending in generally side-by-side spaced apart relation along virtually the full vertical extent of the half-shell member 14 (FIG. 2) with each air bag including an inlet tube 32 adapted to extend through corresponding apertures 24 in the half-shell member 14.

Preferably, the transverse dimensions of the air bags 30 are slightly tapered toward the bottom of the cast 10 to conform more precisely to the similarly tapered contour of the lower leg although this is by no means a necessity. It will be noted furthermore that the maximum lateral extent or dimension of each air bag 30 whether disposed within half-shell member 12 or 14 is substantially less than the transverse inside dimension or circumference of each half-shell member, respectively, or is substantially less than 180° of the transverse circumference of the limb with which it is intended to engage. The actual transverse extent of the individual air bags may vary depending upon the number used, however, when using three such air bags as indicated in FIGS. 1A, 1B, 3 and 4, each air bag preferably extends about 110° with respect to the transverse outer circumference of the limb (or 110° relative to the inner transverse circumference of the assembled cast 10), and is evenly spaced from the others, i.e., each air bag 30 has its centerline spaced approximately 120° from the corresponding centerlines of the other two neighboring air bags.

The pneumatic cells or air bags 30 can be fabricated from any imprevious thin, flexible material so as to be readily inflatable by a suitable medium such as air introduced through the inlet tube or port 32 thereby permitting the air bag to conform to the irregular shape or curvature of the injured limb with which each air cell is intended to engage as will be explained in further detail below. Thin vinyl plastic sheeting is an especially preferred material for the air bags 30 since such material may be cut and folded to shape quite easily and simply heat or ultrasonically sealed along the cut edges in a well-known manner. It will be appreciated, however, that other, thin, impervious, pliable materials such as rubber, coated fabrics, etc. may be used as well.

As schematically indicated by the cross-hatched lines in FIGS. 1A, 1B, and 2, each air cell 30 is preferably entirely encased in a jacket or sleeve 34 of soft absorbtive material fabricated from a woven fabric, or if desired, from non-woven synthetic fibers. Other well-known materials may be employed as well provided they are pliable and are capable of absorbing moisture or the like. The sleeve of absorbtive material provides a sterile surface in contact with the injured limb, helps to cushion the limb when encased within the half-shell members 12, 14, and furthermore facilitates ventilation of the contacted surface of the limb as will be explained more completely in the ensuing discussion.

It has been found that the air bags 30 need not be permanently affixed to the interior surfaces of the shell members 12, 14, but merely placed substantially in the position shown. This is advantageous in that the air bags may easily be replaced and furthermore may have their positions adjusted slightly to meet individual requirements. Of course, if desired, the air bags may be attached to the half-shell members by a light adhesive or similar such means as will occur to those skilled in the art.

As mentioned above, the cast shown in FIGS. 1 – 6 is intended as a walking cast and toward this end, the usual rubber heel member 36 may be attached to the bottom generally flattened surface 38 of the lower horizontally extending foot portion 18 of the half-shell member 14 as best seen in FIG. 2. The heel member 36 is preferably attached to the half-shell member 14 by a pair of threaded fastening elements extending through suitably registering apertures in the half-shell member and heel member respectively. In order to provide comfort to the wearer of the cast, the shell member 14 includes a conventional resilient foot pad 40, whereas the shell member 12 includes a similar resilient pad 42 attached interiorly to the lower horizontally extending portion of the half-shell member and adapted to provide a cushion between this portion of the half-shell member 12 and the instep of the wearer's foot as is also shown in FIG. 2. Resilient foot pads 40, 42 may readily be attached to their respective half-shell members by employing a suitable known adhesive.

Figure 5:
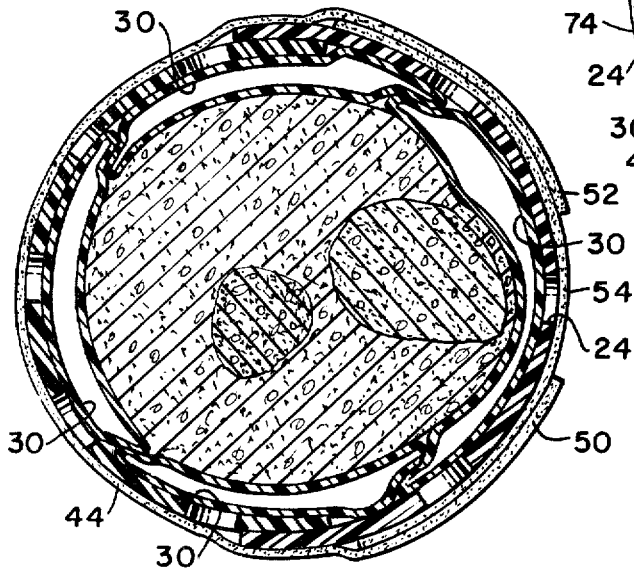
FIG. 5 is a sectional plan view similar to FIG. 3, but showing a slightly modified form of the cast shown in FIGS. 1A, 1B, and 2 - 4.
Figure 6:
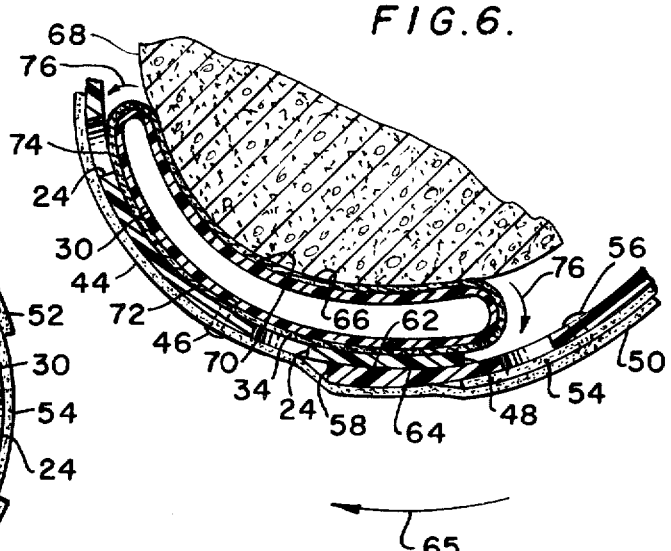
FIG. 6 is an enlarged detail view of a portion of FIG. 3.

For the purpose of releasably securing the half-shell members 12, 14 about an injured limb, closure means are provided preferably in the form of a series of circumferentially extending strips of flexible mating fastening material such as is commercially available under the trademark VELCRO. Half-shell member 14 includes a plurality of such strips 44 whose length is substantially greater than the circumferential extent of the shell member 14 itself. Each strip 44 of fastening material is attached to the exterior surface of the half-shell member 14 by a pair of diametrically opposed rivets 46 located inwardly from each lateral free edge 48 of the shell member 14, respectively, as seen to best advantage in FIG. 6. Each VELCRO fastening strip 44 on the half-shell member 14 thus includes a pair of ends 50, 52 adapted to freely extend beyond the lateral free edges of the shell member 14 (FIG. 1A). Half-shell member 12 carries a corresponding plurality of circumferentially extending VELCRO fastening strips 54 attached to the exterior surface thereof by similar rivet means 56 (see FIG. 6). The circumferential extent of the fastening strips 54 is less than that of the half-shell member 12 and the extremity of each strip 54 terminates at a point displaced inwardly from the free lateral edge 58 of the half-shell member 12 as depicted in FIG. 6. As shown in FIGS. 1A and 1B, there are three fastening strips 44 located at regularly spaced intervals along the vertical or upright portion of the half-shell member 14 and a fourth such strip 44 located on the lower horizontally extending foot portion 18 of the half-shell member 14. It will be noted that the latter fastening strip extends through a slot 66 formed in the heel member 36 between the latter and the lower surface 38 of the horizontally extending foot portion of half-shell member 14 and thus serves to maintain this fastening strip in its intended position (see FIG. 2). Similarly, half-shell member 12 has four fastening strips 54 located in such a manner as to be circumferentially aligned with the fastening strips 44 on the half-shell member 14 when the two half-shell members are in assembled condition as indicated in FIG. 1B. Although four fastening strips are employed in connection with the walking cast of FIGS. 1 – 6, it will be appreciated that this number is not critical and may be varied depending upon the size and type of cast being utilized. Suffice it to say, that a sufficient number of strips are employed at spaced apart distances longitudinally with respect to the cast to prevent buckling of either half-shell member when the two half-shell members are assembled relative to each other and an injured limb as will be explained below.

Figure 4:
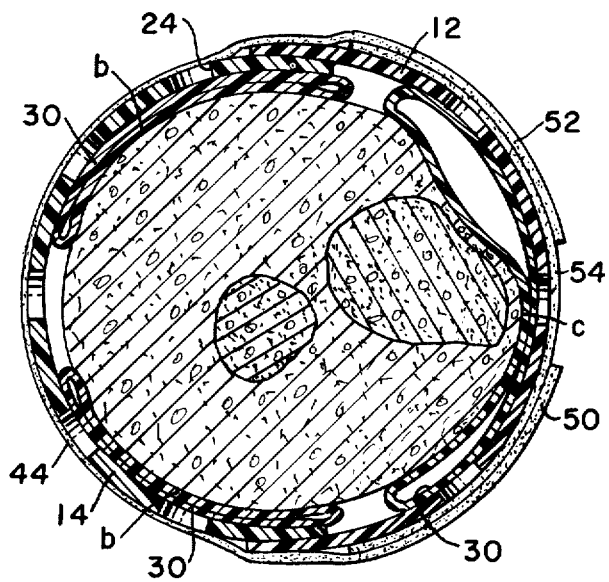
FIG. 4 is a sectional plan view taken along line 4—4 of FIG. 2.

In accordance with the present invention, the walking cast 10 may easily be applied about an injured limb — in the case illustrated the lower leg — by simply placing the limb in the half-shell member 14 as shown in FIG. 2 with the sole of the foot resting on resilient pad 40 and with the back of the heel and the rear portion of the mid-calf in snug abutting contact with the non-inflated air bags 30 as indicated, for example, by the letters a and b (see also FIG. 4). At these areas of contact the leg will abut directly against the air bags 30 which in turn are flattened against and abut directly against the interior surface of the half-shell member 14. In essence, therefore, the leg will be in indirect abutting contact at the areas generally indicated by the letters a and b with the interior surface of the upright portion 16 of the half-shell member 14.

Half-shell member 12 is then held in the position shown in FIG. 1A and fitted relative to the half-shell member 14 by engaging the latter about the injured limb in a radially telescoping manner. That is, the diametrically opposed lateral free edge portions 58 of the half-shell member 12 are flexed slightly outwardly to permit them to overlap and receivably engage the corresponding diametrically opposed lateral free edge portions 48 of the half-shell member 14 with the half-shell member 12 being displaced relative to the half-shell member 14 generally in the direction indicated by arrow 60 in FIG. 6. Such displacement causes the inner surface 62 adjacent each lateral free edge portion 58 of the half-shell member 12 to slide relative to the juxtaposed outer surface 64 adjacent each lateral free edge portion 48 of the half-shell member 14 with the two sliding surfaces in light frictional engagement with one another. The half-shell member 12 is so displaced relative to the half-shell member 14 and the injured limb until the half-shell member 12 assumes the position substantially as shown in FIG. 2 at which position the front or shin bone portion of the leg in the proximity of the mid-calf and the instep of the foot are in snug abutting contact with the flattened air bag 30 and the resilient foot pad 42 as indicated by the letters c and d, respectively, and these parts, in turn, are in abutting contact with the interior surface of the shell member 12. Of course it will be appreciated that due to the irregular shape of the lower leg and the relatively regular shape of the half-shell members 12, 14 direct abutting contact between the leg and the interior surface defined by the inwardly facing portions of the non-inflated, flattened air bags 30 will not occur at several locations within the assembled cast, for example, around portions of the ankle and below and above the mid-calf.

In accordance with the invention, it is desired that there be snug indirect contact or abutting engagement between the lower leg and the two radially telescoped half-shell members at least at one axial or longitudinal location along the leg as, for example, generally indicated by the letters b and c in FIG. 4, and preferably at two spaced axial or longitudinal locations as, for example, generally indicated by the letters a and d on the one hand and b and c on the other hand in FIG. 2 with the two axially or longitudinally displaced locations of snug indirect contact or abutting engagement with the radially telescoped half-shell members preferably straddling the injured portion of the limb. Fulfillment of this requirement is facilitated by the fact that the two half-shell members have the capability of easily being flexed about their central longitudinal axes and therefore are capable of being radially telescoped with respect to each other as mentioned above, and thus the inner diameter of the radially telescoped, substantially cylindrical shell structure formed by the two diametrically opposed concentrically nested half-shell members can readily be selectively adjusted with respect to the limb so as to achieve the aforedescribed snug indirect contacting relationship or abutting engagement independent of the size or irregular shape of the limb.

It will be understood that the term "radially telescoped" as used herein and in the appended claims refers broadly to the situation where a pair of half-shell members are placed in diametrically opposed facing position relative to each other and are concentrically nested relative to each other about a limb or other body part to form a substantially annular shaped hollow structure that is relatively flexible about the longitudinal axis thereof, yet is relatively inflexible about a transverse axis perpendicular to said longitudinal axis. Due to such flexibility the internal diameter of the resulting annular shaped structure may be selectively adjusted e.g., made smaller, by flexing the two half-shell members about the common longitudinal axis thereof and simultaneously radially displacing the half-shell members relative to each other and the encased limb. The term "radially telescoped" is thus to be distinguished from the meaning usually ascribed to the term "telescoped" which implies the concentric nesting of an annular member of a given diameter within another annular member of a greater diameter by the longitudinal or axial displacement of the first mentioned annular member relative to the second mentioned annular member or vice versa.

Thus, by providing half-shell members 12 and 14 which are flexible about their longitudinal axes respectively, and permitting each half-shell member's lateral free edge portions to slidably engage one another in overlapping relation as shown in FIG. 6, the resulting substantially cylindrically shaped shell structure formed by the interengagement of the two half-shell members 12, 14 can be adjusted relative to the injured limb encased therein simply by radially flexing each half-shell member and permitting more or less relative displacement between juxtaposed surfaces 62, 64 in the direction of the arrow 65. Hence, half-shell members of a single standard size can be employed and adjusted to fit a wide range of varying sized corresponding limbs, or can be adjusted from time to time during the period of immobilization to conform to the changing size of a particular limb, the range of adjustment depending only upon the extent to which the lateral free edge portions of each half-shell member may be flexed about each member's longitudinal axis respectively, and surface 62 on each lateral portion of the half-shell member 12 is permitted to slide relative to the other half-shell member's corresponding surface 64 in the direction of the arrow 65.

In the prior art air-suspension cast employing a two-part outer protective shell such adjustment in the outer shell structure cannot be made because the corresponding lateral free edges of the two half-shell member parts are directly in abutting relation with one another and the half-shell members are rigid rather than being flexible as in the present invention.

When the two half-shell members 12, 14 are engaged with each other in a radially telescoping manner and are in snug indirect contacting relation or abutting engagement with the injured limb at the preferred spaced apart axial or longitudinal locations with respect to the injured limb as described above, the half-shell members 12, 14 may be fixed in position relative to each other and the encased limb by attaching the freely extending ends 50, 52 of the VELCRO fastening strips 44 on half-shell member 14 to the corresponding VELCRO fastening strips 54 on the half-shell member 12 as substantially shown in FIGS. 1B, and 3 – 6. The resulting radially telescoped shell structure so formed will provide a protective casing or column circumscribing the injured limb that inherently is extremely rigid about a transverse axis perpendicular to the longitudinal axis of the casing, and as explained above will be in indirect snug abutting transverse contact with the injured limb at at least two axially or longitudinally displaced locations thereby preventing relative displacement of the injured limb with respect to the radially telescoped shell structure or protective casing.

In passing it will be noted that the radially flexed diametrically opposed lateral portions of each half-shell member 12, 14 will tend to return to their normal unflexed positions and this condition will produce a biasing or spring-force in the radial direction sufficient to maintain a firm frictional engagement between the corresponding overlapping engaged surfaces of the two half-shell members (FIG. 6). This frictional gripping engagement, in turn, helps to maintain the two cooperatively engaged half-shell members in their adjusted relative position during engagement of fastening strips 44, 54 and moreover, is helpful in preventing relative displacement of the two engaged half-shell members in a direction parallel to the longitudinal axis of the shell structure (i.e., in a direction normal to the plane of the paper as viewed in FIG. 6) after the fastening strips 44, 54 have been engaged and the shell structure fitted about the injured limb.

After the half-shell members 12, 14 has been assembled as shown in FIG. 1B, and as described above, air or other suitable inflation medium is then introduced into each air bag 30 through their respective inlet tubes 32 to cause the air bags to inflate. Sufficient internal pressure is developed in each air bag to completely fill the annular spaces or voids existing between the inwardly facing sides or portions of the air bags and the relatively irregularly contoured surface of the injured limb as shown, for example, in FIGS. 2 and 3. Inflation of the flexible air bags 30 causes them to conform to the portions of the limb not in indirect abutting contact with the interior surface of the shell structure and thereby provides firm constant pressure support for these portions of the limb. In addition, such inflation renders the outer radially telescoped shell structure extremely rigid with respect to further flexural displacement about the shell structure's longitudinal axis. Since each air bag 30 has a relatively small interior volume, and the air bags are confined between the outer shell structure and the encased limb, relatively low inflation pressures ranging from about 15 to about 25 mm. Hg. have been found to provide unexpectedly firm support. Thus, by employing as few as three air bags at spaced intervals about the circumference of the limb as indicated in FIG. 3, a three-point suspension may be achieved capable of completely immobilizing an injured limb encased within the radially telescoped shell structure.

Moreover, it will be noted in accordance with an important feature of the present invention that despite inflation of the air bags 30 as described above, the portions of the immobilized limb originally in indirect snug abutting contact with the interior of the telescoped shell structure will virtually retain their indirect snug abutting contacting relation with the interior surface of the two radially telescoped half-shell members. This is shown to best advantage in FIG. 4, where the air bags 30 although under internal pressure remain virtually unextended in the radial direction at their circumferential locations directly and oppositely in engagement with the transverse portions of the immobilized limb as indicated, for example, by the letters b and c. In contrast, the inflated air bags do extend radially to fill the voids between those portions of the limb not in indirect contact or abutting engagement with the interior of the radially telescoped shell structure as clearly shown in FIGS. 2 – 4. Since, as mentioned above, the immobilized limb always remains in virtual indirect contact or abutting engagement with the interior surface of the cylindrical shell structure formed by the two radially telescoped half-shell members 12, 14 at at least one axial or longitudinal location and preferably at two displaced axial or longitudinal locations, the damaged limb is prevented from being moved or displaced relative to or within the shell structure and thus, in effect, the cylindrical shell structure itself as well as the circumferential array of air cushions provided by the inflated air bags 30 contribute to immobilization of the injured limb whereas heretofore prior art casts of the type described herein have depended only upon an annular air cushion to effect such immobilization.

Figure 3:
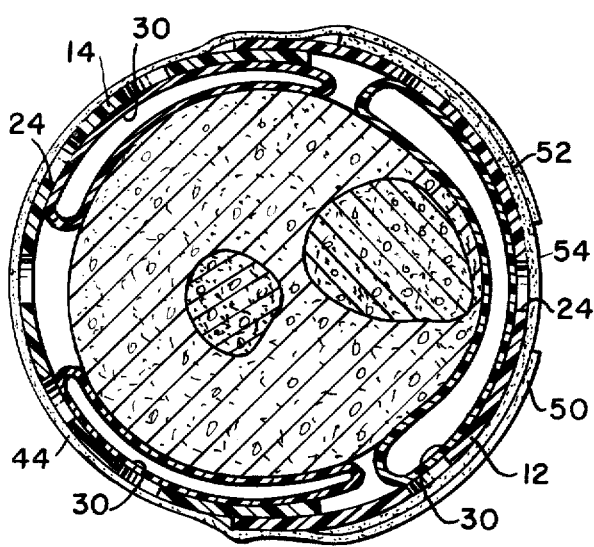
FIG. 3 is a sectional plan view taken along line 3—3 of FIG. 2.

Furthermore, by providing more than two air cells where each air cell or air bag 30 has a transverse dimension substantially less than the transverse inside circumference of each half-shell member respectively (or substantially less than 180° of the transverse circumference of the the injured limb) as shown in FIG. 3, for example, the lateral extremities of the inflated air cells as well as their central portions have been found to be relatively dimensionally stable in response to radially applied compressive loads imposed thereon by the injured limb thereby contributing toward the excellent stability of the immobilized limb within the radially telescoped outer structure especially with regard to preventing lateral displacements of the limb relative to the outer shell.

Similarly, it will be understood that the action of maintaining the radially telescoped half-shell members in indirect snug contact or abutting engagement with the injured limb after inflation of the air bags 30 whether such contact or abutting engagement occurs at one axial location or at several axial or longitudinal locations along the limb serves to maintain each inflated air cell dimensionally stable with respect to its longitudinal or axial extent and thus effectively prevents relative rotational displacement of the limb about a transverse axis perpendicular to the longitudinal axis of the outer shell structure.

As previously explained, the preferred arrangement of three air bags 30 nested within the radially telescoped shell structure in circumferentially spaced apart relationship as depicted in FIGS. 3 and 4 is further advantageous in that it permits placement of the individual air bags 30 to be adjustably varied relative to one another to assure optimum comfort to the wearer of the cast. In addition, the apertures 24 in the half-shell members 12, 14 permit unimpeded circulation of air into the interior of the cast and into direct contact with the limb's skin surface exposed between the spaced apart air bags. This permits the skin to breathe freely reducing surface heat and perspiration, and in general, further enhances the wearer's comfort. Nonetheless, it may be desirable especially during the early stages of immobilization when edema due to the original injury is present, to completely surround the injured limb with a constant pressure supporting surface in engagement therewith. Accordingly, as shown in FIG. 5, an additional air bag 30 may be placed in nesting position within the shell structure formed by the two interengaging radially telescoping half-shell members and the four air bags emplaced such that the lateral edge of each air bag slightly overlaps the adjacent lateral edge of its neighboring air bag. By this alternatively preferred arrangement the entire annular space between the interior surface of the encased limb is occupied by the overlapping air bags and a multi-cellular constant pressure supporting surface is provided completely surrounding and engaging the injured limb. Of course, it will be appreciated in connection with FIG. 5 that as in the case where only three air bags are provided in circumferentially juxtaposed position (FIG. 3), at least one and preferably two axially or longitudinally displaced portions of the injured limb still will virtually remain in indirect contact or abutting engagement with the interior wall surface of the shell structure as indicated, for example, by the letters a, b, c, and d in FIG. 2 and the letters b and c in FIG. 4.

It will be recalled in accordance with the present invention that each individual air bag 30 includes an outer sleeve or covering 34 of absorbtive material. Referring to FIG. 6, the manner in which such absorbtive outer sleeve in conjunction with the apertures 24 provided in each half-shell member 12, 14 function to afford excellent ventilation of the interior of the cast will now be explained. As clearly shown in FIG. 6, inflation of each air bag 30 causes the laterally inwardly facing portion 66 of its corresponding outer sleeve 34 to directly engage in conforming relation a coextensive portion of the exterior skin surface 68 of the immobilized limb. Since the inwardly facing portion 66 of the air bag's absorbtive outer sleeve is quite firmly urged against the skin surface 68 owing to the internal pressure of the air bag, normal body heat is prevented from being transferred away from that portion of the skin surface 68 in contact with the air bag's outer absorbtive sleeve. As a result normal evaporative cooling is prevented and liquid perspiration rapidly collects and remains trapped between the air bag outer sleeve and the surface of the limb with which it is in contact. Unless removed such trapped perspiration can eventually cause irritation of the skin and/or discomfort to the wearer of the cast. As taught in the prior art disclosure the provision of an absorbtive liner on the inner surface of the inflatable air bag may be effective to absorb such perspiration. However, it has been found that when the absorbtive liner extends only along the inner surface of the inflatable air bag, it quickly becomes saturated and can no longer absorb any further perspiration which because of natural body processes is continuously being produced. In contrast, it will be observed in FIG. 6 that the absorbtive sleeve 34 contemplated by the present invention not only extends along the inwardly facing surface 70 of each air bag but completely surrounds the air bag and thus extends along the outwardly facing surface 72 of the air bag as well. Due to this arrangement, the outwardly facing portion 74 of the absorbtive sleeve on each air bag is directly disposed in juxtaposed relation with regard to the apertures 24 in either half-shell members 12 or 14 as the case may be. Hence, the liquid perspiration absorbed by the inwardly facing portion 66 of the sleeve 34 is urged to flow, by wicking action along the directions indicated by arrow 76 into the region of the outwardly facing portion 74 of the sleeve 34 where it is easily evaporated off due to the latter portion of the protective sleeve being in direct proximity to the apertures 24. In affect, therefore, by providing a sleeve 34 of absorbtive material completely encircling each air bag 30 as shown in FIG. 6, an uninterrupted flow path is provided for continuously transferring liquid perspiration from the portion of the skin surface 68 engaged by each air bag outer sleeve to the vicinity of the apertures 24 where the perspiration is evaporated off thereby preventing its accumulation and consequent irritation of the skin surface and/or discomfort to the wearer of the cast.

Although the walking cast described above is intended to protect and immobilize the foot and the lower leg up to a point immediately below the knee, it may obviously be modified to extend above the knee i.e., beyond the lower leg. Nor is the invention to be limited exclusively to walking casts as such. Thus, cast 10 may with only slight modification and without departing from the invention be adapted for the treatment of limbs or other parts of the body such as the lower arm, the upper arm, the upper thigh, and so on.

Moreover, orthopedic devices constructed in accordance with the present invention may be applied to the treatment of damaged or injured joints interconnecting a pair of limbs or other body parts. To illustrate this, a further modified alternatively preferred form of the invention intended for immobilizing a damaged or injured joint interconnecting a pair of articulated limbs or body members will now be described in connection with FIGS. 7 – 9, in particular, a knee brace for immobilizing a damaged knee joint connecting the thigh and lower leg.

As schematically shown, knee brace 110 comprises a pair of complementary, interengaging half-shell members 112, 114, each generally having a channel shaped or semi-cylindrical cross-sectional configuration for conforming to the lower portion of the thigh and the upper portion of the lower leg. Since the cross-sectional dimension of the thigh at the location engaged by the upper extremities of the two shell members 112, 114 is usually appreciably greater than the cross-sectional dimension of the calf engaged by the lower extremities of the two half-shell members, the latter are preferably formed having a gradual taper in their inside diameter i.e., from a maximum at their upper extremities to a minimum at their lower extremities. Additionally, for increased comfort, the two half-shell members 112, 114 are preferably slightly curved substantially at their mid-sections respectively to accommodate the leg in a slightly flexed condition as indicated in FIG. 7.

Nested interiorly within the knee brace formed by the interengaging half-shell members 112, 114 is a pair of flattened arcuately extending air cells or air bags 116 each preferably having a valved inlet port 118 communicating with the exterior of the shell member 114 through a suitable aperture provided therein (not shown). Air bags 116 are preferably positioned in a diametrically opposed manner along the lateral portions of the leg engaged by the knee brace as best seen in FIG. 8 with each air bag extending longitudinally along the interior surface of the knee brace from a position above the knee to a position below the knee as shown in FIG. 7. In order to improve the stability of each air cell or bag 116 when inflated, the longitudinal dimensions thereof are substantially less than the longitudinal dimension of each half-shell member 112, 114;

and in particular, are preferably about one-half the longitudinal extent of each half-shell member. To conform to the gradual taper in inside diameter of the two shell members 112, 114, the transverse dimension of each air bag 116 preferably is gradually tapered from a maximum at the upper extremity thereof above the knee to a minimum at the lower extremity thereof below the knee as is also generally indicated in FIG. 7. In addition, the transverse dimension of each air cell 116 measured along any given transverse plane is substantially less than the transverse inside circumference of each half-shell member respectively, and preferably is adapted to extend about 110° with respect to the transverse outer circumference of the limb at the axial location defined by said given transverse plane. When inflated, the air bags are adapted to extend radially so as to fill the voids between the sides of the leg and the interior of the knee brace formed by interengagement of the two half-shell members as indicated in FIG. 8 and as will be described below.

Figure 7:
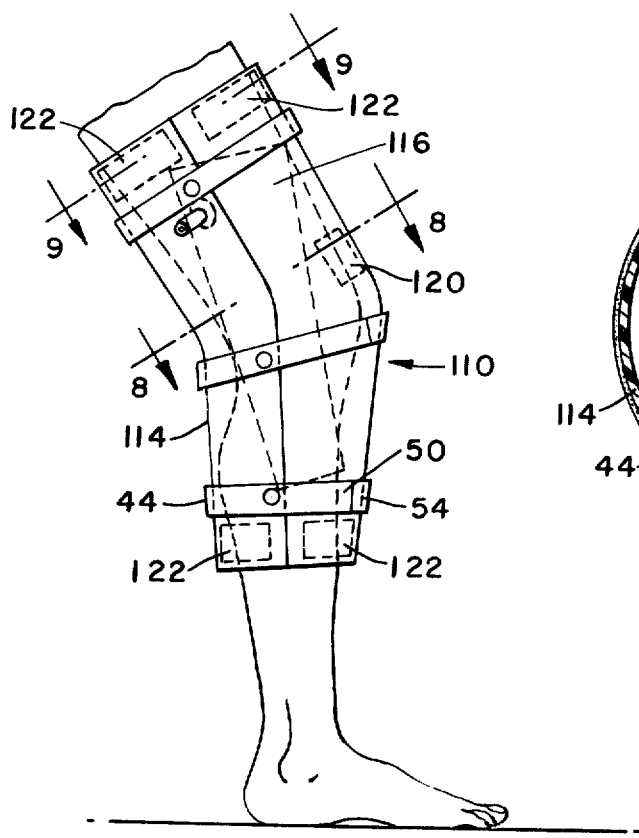
FIG. 7 is a schematic side view in elevation of an alternate preferred embodiment of the present invention, namely, a knee brace, showing the latter in engagement with a leg.
Figure 8:
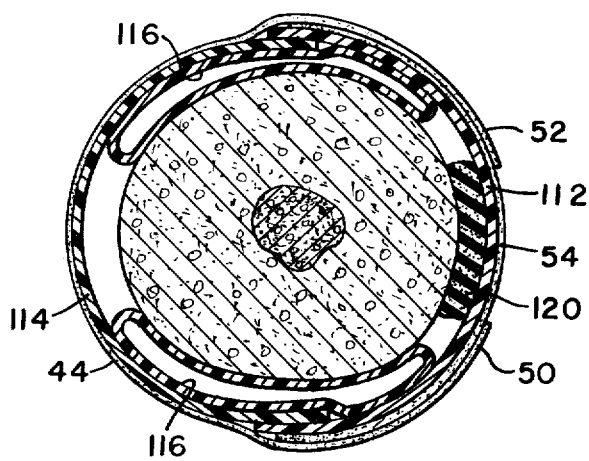
FIG. 8 is a sectional plan view taken along line 8—8 in FIG. 7.

A pad 120 preferably of resilient sponge rubber or the like material is affixed to the interior of the half-shell member 112 by suitable adhesive means in position to abut and directly engage the front portion of the leg immediately above the knee cap as depicted in FIGS. 7 and 8. The sponge rubber pad 120 helps to maintain the leg in a fixed position within the knee brace and prevent motion of the knee relative to and within the brace. Alternatively, an air bag (not shown) of substantially the same size and shape as the resilient sponge rubber pad 120 may be used instead.

Figure 9:
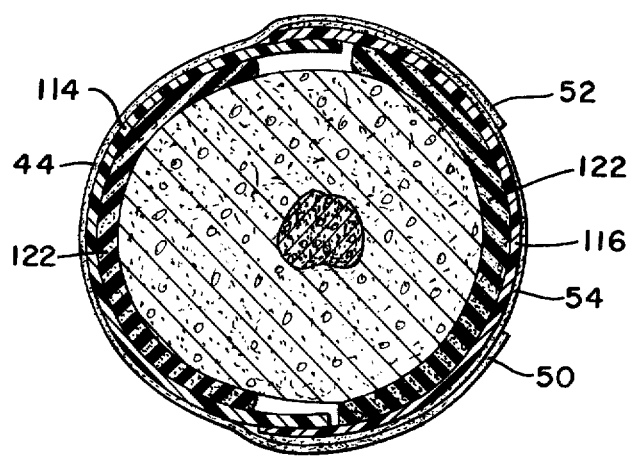
FIG. 9 is another sectional plan view taken along line 9—9 in FIG. 7.

For additional comfort, each half-shell member 112, 114 may be provided with an arcuately shaped cuff member 122 of similar sponge rubber material fixed interiorly thereof at either extremity as shown in FIGS. 7 and 9 since it is at these locations that the interior of half-shell members 112, 114 are in snug abutting peripheral contact with the thigh and lower leg, respectively. Here again, however, air bags (not shown) of substantially the same size and shape may be used in place of the resilient sponge rubber cuff members 122.

A plurality of cooperatively engaging VELCRO fastening strips 44, 54 as described above in connection with the walking cast of FIGS. 1 – 6 may be employed in the manner indicated in FIGS. 7 – 9 to releasably secure the half-shell members 112, 114 in relative engaged position about the encased leg. Of course, it will further be appreciated that each half-shell member 112, 114 may, if desired, also include the apertures 24 and similarly, the absorbtive surrounding sleeve 34 in conjunction with each air bag 116, although these parts have not been shown in FIGS. 7 – 9 for the sake of brevity.

Moreover, half-shell members 112, 114 are preferably formed of the same tough, thin, radially flexible material as are the previously described half-shell members 12, 14 and thus are adapted to be fitted about the leg in substantially the same manner. That is, initially the leg is placed in the shell member 114 with two longitudinally displaced portions of the leg, namely, the rear of the thigh and the rear of the mid-calf in snug abutting contact with the arcuate resilient cuff members 122 generally located at the remote opposite extremities of the half-shell member. Next, the uninflated, flattened air bags 116 are disposed in their preferred diametrically opposed, lateral positions relative to the leg as shown, for example, in FIGS. 7 and 8. Half-shell member 112 is then positioned diametrically opposite to half-shell member 114 and displaced relative to the latter and the leg for engagement therewith in a radially telescoping manner, i.e., the free lateral edge portions of half-shell member 112 are flexed outwardly for receivably engaging the free lateral edge portions of shell member 114, and the corresponding lateral edge portions of the shell members 114, 112 are slid relative to each other in overlapping frictional engagement until the two resilient arcuate cuff members 122 and the resilient pad 120 on the half-shell member 112 snugly and firmly engage the leg. Recalling that in accordance with the invention, the half-shell members are relatively flexible about their longitudinal axis respectively, half-shell members 112, 114 may readily be radially telescoped relative to each other to achieve a firm contacting circumferential relationship with the leg at least at the remotely disposed extremities of the half-shell members, such snug contacting circumferential engagement being shown to good advantage in FIG. 9.

The two-shell members 112, 114 are then fastened relative to one another and the encased leg by attaching the freely extending portions of the VELCRO fastening strips 44 carried by the half-shell member 114 to the circumferentially aligned VELCRO fastening strips 54 located on shell member 112 substantially as shown in FIGS. 7 – 9. Finally, the air bags 116 are inflated to provide a pair of constant pressure supporting surfaces on either side of the knee (and above and below the knee) which in conjunction with the resilient cuffs 122, and the resilient pad 120 engaging the front of the leg immediately above the knee cap, firmly lock the thigh and lower leg in the slightly flexed condition shown in FIG. 7. Hence, the thigh is prevented from moving relative to the lower leg and vice versa, and the damaged or injured knee joint interconnecting these articulated body members is completely immobilized.

As is apparent from the above disclosure of the alternatively preferred embodiments of FIGS. 1–6 and of FIGS. 7–9, in practicing the present invention it is not necessary that the interior surface of the tubular outer half-shell members contact or engage corresponding portions of the encased body part indirectly through the air bags (i.e., at axial or longitudinal locations coextensive with flattened portions of the air bags); but, alternatively, may contact or engage corresponding portions of the encased limb directly at axial locations beyond the longitudinal extent of the air bags such as clearly disclosed, for example, at location "*d*" in FIG. 2, or in connection with the embodiment of FIGS. 7–9 where the interior surface of the tubular outer half-shell members peripherally contact or engage the encased body part at respective axial or longitudinal locations spaced above and below the air bags 116. Thus, it is to be understood that the terms "engage in an abutting manner", "in abutting engagement", or the like, as used in the appended claims are to be broadly construed to cover situations where there is direct contact or engagement between the interior surface of the tubular outer shell member and corresponding portions of the encased body part; or alternatively, where there is indirect contact or engagement between the interior surface of the tubular outer shell member and corresponding portions of the encased body part through coextensive portions of the flattened air bags or resilient pads or cuffs; or alternatively, where there are combinations of the foregoing.

While particular preferred embodiments of the present invention have been disclosed hereinabove as required by statute, many modifications within the spirit and scope of the invention may be made. For example, instead of utilizing an inflatable pneumatic cell or air bag that includes an inlet port and/or valve means through which a pressurizing medium may be admitted after the radially telescoped half-shell members have been fitted about a body part, it is anticipated that a completely sealed air bag inflated to a pre-determined internal pressure prior to such installation may be used as well although this may require slightly more skill and care when fitting the half-shell members about the injured body part. Similarly, instead of using fastening strip members fabricated from VELCRO fastening material, other conventional fastening devices may be employed to releasably secure the half-shell members together such as, for example, belt and belt buckles, adhesive tape, and so on. Obviously, still other changes in the details of construction, and arrangement of parts may also be made without departing from the invention as defined in the accompanying claims, and accordingly, all equivalents, alterations, and modifications within the spirit and scope of the present invention are herein meant to be included.

What is claimed is:

1. Orthopedic apparatus for immobilizing a body part comprising:
   a pair of complementary half-shell members, each of said half-shell members being generally channel shaped in transverse cross-section and having a pair of radially spaced, longitudinally extending opposed free edges,
   said shell members being relatively rigid about an axis lying in planes defining said transverse cross-section and being relatively flexible about an axis substantially perpendicular to said first-mentioned axis whereby the opposed radially spaced free edges of each half-shell member are adapted to be flexed relative to one another to selectively decrease or increase the inside diameter of each said half-shell member respectively,
   said shell members adapted to be fitted relative to each other about said body part in a substantially diametrically opposed manner with the opposed radially spaced free edges of said half-shell members being concentrically nested to define a radially telescoped tubular outer member surrounding said body part and generally conforming to the shape thereof,
   said half-shell members being radially telescopingly adjusted relative to each other about said body part such that separate longitudinally spaced portions of the inner surface of each of said half-shell members are adapted to engage said part in an abutting manner at corresponding longitudinally spaced locations along said body part respectively,
   said half-shell members including means for releasably securing same together in said adjusted radially telescoped relation; and
   a plurality of pneumatically inflated cells disposed within said half-shell members in a circumferentially juxtaposed manner, said inflated cells extending longitudinally with respect to said half-shell members and adapted to extend radially inwardly between the interior surface of said tubular outer member and said body part, at least portions of the radially inner extent of said inflated cells adapted to conform to and engage corresponding portions of said body part which are spaced radially inwardly from said interior surface of said tubular outer member and which are not in abutting engagement with said interior surface of said tubular outer member whereby said inflated cells provide immobilizing support for said corresponding portions of said body part, and said radially telescoped tubular outer member provides additional immobilizing support for said body part by virtue of engaging said body part in said abutting manner at said plurality of separate longitudinally spaced locations as hereinaforesaid.

2. The apparatus of claim 1 wherein the action of said half-shell members engaging said corresponding portions of said body part in said abutting manner at said separate longitudinally spaced locations maintain those portions of said inflated cells coextensive with said locations in a substantially flattened condition.

3. The apparatus of claim 1 wherein said pneumatically inflated cells have an internal pressure within the range of 15 mm Hg to 25 mm Hg.

4. The apparatus of claim 1 wherein said body part comprises the lower leg and foot of a human, one of said half-shell members being L-shaped to generally conform to the back of the lower leg and underlie the heel and sole of the foot, the other of said half-shell members being L-shaped to conform generally to the front of the lower leg and overlie the instep portion of the foot, and wherein the inner surface of said one half-shell member is adapted to engage said body part at separate longitudinally spaced locations in an abutting manner including the back of the lower leg and the heel and the sole of the foot, and the inner surface of said other half-shell member is adapted to engage said body part at separate longitudinally spaced locations in an abutting manner including the front of the lower leg and the instep of the foot whereby said orthopedic apparatus is employable as a walking cast.

5. The apparatus of claim 1 wherein said body part comprises a first limb and a second limb and a joint connecting said first and second limbs, and wherein the inner surface of said one half-shell member is adapted to engage said body part in an abutting manner at separate longitudinally spaced locations on said first and said second limb respectively, and wherein the inner surface of said other half-shell member is adapted to engage said body part in an abutting manner at separate longitudinally spaced locations on said first and second limb respectively, whereby said orthopedic apparatus is employable to immobilize said first limb relative to said second limb.

6. The apparatus of claim 1 wherein said means for releasably securing said half-shell members together comprises a plurality of fastening members longitudinally spaced along the outer surface of said tubular outer member, each of said fastening members including a first flexible fastening strip affixed exteriorly to said one half-shell member and a second flexible fastening strip affixed exteriorly to said other half-shell member in circumferential alignment with said first fastening strip, said first fastening strip having a pair of end portions respectively extending beyond the radially spaced free edges of said one half-shell member, said second fastening strip having a pair of end portions terminating respectively in spaced relation with respect to the radially spaced free edges of said other half-shell member respectively, said end portions of said first fastening strip being in fastening mating engagement with said terminal end portions of said second fastening strip, respectively, when said half-shell members are secured together in said adjusted radially telescoped relation about said body part.

7. The apparatus of claim 1 wherein each of said plurality of inflated cells comprises an inflatable flexible bag including valve means for permitting a pressurizing medium to be introduced therein and for maintaining said pressurizing medium within said inflatable bag at a predetermined internal pressure.

8. The apparatus of claim 7 wherein said predetermined internal pressure is within the range of 15 mm Hg to 25 mm Hg.

9. The apparatus of claim 1 wherein said plurality of inflated cells comprises three in number, and said cells are disposed within said tubular outer member in circumferentially spaced relation from one another.

10. The apparatus of claim 1 wherein said plurality of inflated cells comprises four in number, said inflated cells being disposed within said tubular outer member such that the opposed lateral extremities of each cell respectively slightly overlap a lateral extremity of a neighboring cell to define a multi-cellular supporting surface adapted to completely circumferentially surround said body part.

11. The apparatus of claim 1 wherein said plurality of inflated cells comprises two in number, said cells being disposed within said tubular outer member in a diametrically opposed manner between the diametrically opposed seams of said tubular outer member and the outer surface of said body part respectively, said seams being defined by the telescoping radially spaced free edges of said half-shell members.

12. The apparatus of claim 7 wherein at least one of said flexible bags includes an outer sleeve of absorbtive material extending substantially completely circumferentially around said one bag so that a portion of said outer sleeve is adapted to contact the surface of said body part and a circumferentially corresponding portion of said outer sleeve contacts the inner surface of said tubular outer member, each of said half-shell members being provided with a plurality of spaced apertures, said circumferentially corresponding portion of said outer sleeve being in registration with at least some of said spaced apertures whereby perspiration on said surface of said body part is absorbed by said outer sleeve and caused to wick to said circumferentially corresponding portion of said outer sleeve and be evaporated off through said apertures in registration therewith.

13. The method of immobilizing a body part with the aid of orthopedic apparatus comprising first and second channel shaped shell members each of which has a longitudinal axis substantially parallel to the longitudinal axis of said body part, each of said first and said second shell members being relatively flexible about said first-mentioned axis and being relatively rigid about a transverse axis substantially perpendicular to said first-mentioned axis, means for releasably securing said first and second shell members together about said body part, and a plurality of individual longitudinally extending inflatable support members disposed interiorly with respect to said first and second shell members in circumferentially juxtaposed relation with respect to each other; wherein said method comprises the following steps:

a. fitting said first and said second shell members relative to each other about said body part in a substantially diametrically opposed radially telescoping manner with said first and said second channel shaped shell members forming a tubular outer member surrounding said body part and with said plurality of individual support members being disposed in said circumferentially juxtaposed relation between the inner surface of said tubular outer member and the outer surface of said body part in an uninflated substantially flattened condition;

b. adjustably radially telescoping said first and said second shell members relative to each other to cause separate longitudinally spaced portions of the inner surface of each of said first and second shell members to engage said body part in an abutting manner at corresponding longitudinally spaced locations along said body part respectively;

c. employing said releasably securing means to releasably secure said first and second shell members together about said body part and maintain them in said adjusted radially telescoped position; and d. inflating said inflatable support members to a predetermined internal pressure to cause said inflatable support members to expand radially between the interior surface of said tubular outer member and the exterior surface of said body part so that said inflatable support members conform to and engage corresponding portions of said body part which are radially inwardly spaced from said interior surface of said tubular outer member and which are not in abutting engagement with said tubular outer member.

14. The method of claim 13 wherein only certain portions of said inflatable support members are caused to expand radially through the manipulation as defined in step (d) while certain other portions of said inflatable support members are maintained in their substantially flattened condition by the action of said first and second shell members being brought into abutting engagement with said body part as defined in step (b).

15. The method of claim 13 wherein said step (d) of inflating said inflatable support members to a predetermined internal pressure comprises admitting a fluid medium to the interior of said support members under a pressure within the range of 15 mm Hg to 25 mm Hg.

16. The method of claim 13 wherein said body part comprises the lower leg and foot of a human, said first shell member being L-shaped to conform generally to the back of the lower leg and underlie the heel and sole of the foot, and said second shell member being L-shaped in a complementary manner with respect to said first shell member to conform generally to the front of the lower leg and overlie the instep portion of the foot, further comprising the step of employing said orthopedic apparatus as a walking cast.

17. The method of claim 13 wherein said body part comprises the lower leg and foot of a human, said first shell member being L-shaped to conform generally to the back of the lower leg and underlie the heel and sole of the foot, and said second shell member being L-shaped in a complementary manner with respect to said first shell member to conform generally to the front of the lower leg and overlie the instep portion of the foot, wherein said step (b) comprises engaging said body part with said interior surface of said first shell member in an abutting manner at separate longitudinally spaced locations including the back of the calf, and the heel and sole of the foot; and comprises engaging said body part with said interior surface of said second shell member in an abutting manner at separate longitudinally spaced locations including the front of the calf and the instep of the foot.

18. The method of claim 13 wherein said body part comprises a first limb and a second limb and a joint connecting said first and second limbs, said step (b) comprises engaging said body part with said interior surface of said first shell member in an abutting manner at separate longitudinally spaced locations on said first and second limb respectively; and comprises engaging said body part with said interior surface of said second shell member in an abutting manner at separate longitudinally spaced locations on said first and second limb respectively; further comprising the step of employing said orthopedic apparatus to immobilize said first limb relative to said second limb.

* * * * *

UNITED STATES PATENT AND TRADEMARK OFFICE
CERTIFICATE OF CORRECTION

PATENT NO. : 3,955,565
DATED : May 11, 1976
INVENTOR(S) : Glenn W. Johnson, Jr.

It is certified that error appears in the above-identified patent and that said Letters Patent are hereby corrected as shown below:

First page, in the column of "References Cited", under FOREIGN PATENTS OR APPLICATIONS add the following:

--60,614   3/68   East Germany...128/DIG.20

817,521  7/59   United Kingdom...128/DIG.20--.

Column 2, line 26; after the word "may" insert --not--.

Column 14, line 4; change "affect" to --effect--.

Signed and Sealed this

Eighteenth Day of January 1977

[SEAL]

Attest:

RUTH C. MASON
Attesting Officer

C. MARSHALL DANN
Commissioner of Patents and Trademarks